(12) United States Patent
Rothrock et al.

(10) Patent No.: US 8,685,461 B2
(45) Date of Patent: Apr. 1, 2014

(54) NANOPARTICLE FABRICATION METHODS, SYSTEMS, AND MATERIALS

(71) Applicant: The University of North Carolina at Chapel Hill, Chapel Hill, NC (US)

(72) Inventors: Ginger D. Rothrock, Durham, NC (US); Benjamin W. Maynor, Durham, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 13/915,322

(22) Filed: Jun. 11, 2013

(65) Prior Publication Data

US 2013/0344118 A1 Dec. 26, 2013

Related U.S. Application Data

(60) Division of application No. 11/879,746, filed on Jul. 17, 2007, now abandoned, and a continuation-in-part of application No. PCT/US2006/023722, filed on Jun. 19, 2006.

(60) Provisional application No. 60/831,372, filed on Jul. 17, 2006.

(51) Int. Cl.
*A61K 9/14* (2006.01)

(52) U.S. Cl.
USPC .......................................................... 424/489

(58) Field of Classification Search
None
See application file for complete search history.

(56) References Cited

U.S. PATENT DOCUMENTS

2007/0009564 A1* 1/2007 McClain et al. .............. 424/423
2009/0028910 A1* 1/2009 DeSimone et al. ........... 424/401

* cited by examiner

*Primary Examiner* — Robert A Wax
*Assistant Examiner* — Danah Al-Awadi
(74) *Attorney, Agent, or Firm* — Morgan, Lewis & Bockius LLP

(57) ABSTRACT

Nanosized particles are molded from granules of organic substances in nano-scale molds. The nano-scale molds can be fabricated from non-wetting, low surface energy polymeric materials. The nanosized particles can be virtually any shape, are typically less than 500 micrometers in a broadest dimension, and can include pharmaceutical compositions, biologic drugs, drug compositions, organic materials, and the like.

11 Claims, 2 Drawing Sheets

NANOPARTICLE FABRICATION METHODS, SYSTEMS, AND MATERIALS

CROSS REFERENCE TO RELATED APPLICATIONS

This application is a divisional of U.S. patent application Ser. No. 11/879,746, filed Jul. 17, 2007, which claims priority to U.S. Provisional Patent Application Ser. No. 60/831,372, filed Jul. 17, 2006, and which is a continuation-in-part of PCT International Patent Application Serial No. PCT/US06/23722, filed Jun. 19, 2006, each of which is incorporated herein by reference in its entirety.

INCORPORATION BY REFERENCE

All documents referenced herein are hereby incorporated by reference as if set forth in their entirety herein, as well as all references cited therein, including U.S. Pat. Nos. 4,353,977; 4,352,874; 4,356,257; 4,359,526; and 4,663,274.

TECHNICAL FIELD

Generally, this invention relates to micro and/or nano scale particle and its fabrication. More specifically, the organic particles are formed from solid substances reconstituted into micro and/or nano scale particles having a predetermined geometric shape and size.

BACKGROUND

There has been much interest recently in synthesizing nanometer sized particles because of their potential applications in materials sciences and therapeutics. The formation of these particles can occur through a number of techniques, varying from polymerization to dissolution and precipitation, oxidation and reduction, as well as coalescence. Current techniques begin with a liquid state or a solid material dissolved in a solvent, then the dispersed phase is quenched to a solid state and the continuous phase and solvent are removed to produce the nanoparticles, such as disclosed in U.S. Pat. Nos. 7,018,657 and 6,932,983. Solid materials have also been coalesced into micro or nanometer sized particles by heating, dissolving, reducing, or otherwise treated to form a colloid of interest, such as described in U.S. Pat. Nos. 4,359,526; 6,755,886; and 7,087,523 as demonstrative examples.

These methods of treating solids and forming organic and inorganic nano and microstructures are difficult to control, resulting in irregular colloids with high dispersity.

SUMMARY

According to some embodiments, a composition includes a plurality of particles, each particle of the plurality of particles having a predetermined shape, where each particle of the plurality of particles is derived from a solid substance positioned in a mold cavity, where the plurality of particles has a substantially uniform size distribution; and each particle of the plurality of particles has a broadest dimension of less than about 500 µm. In some embodiments, the plurality of particles have a normalized size distribution of between about 0.80 and about 1.20, between about 0.90 and about 1.10, between about 0.95 and about 1.05, between about 0.99 and about 1.01, between about 0.999 and about 1.001. According to some embodiments, each particle of the plurality of particles is substantially uniform in a linear size, a volume, a three dimensional shape, surface area, mass, or geometric shape. In some embodiments, the particles are organic particles.

According to some embodiments, a nanosized particle includes a drug composition formed into a particle from a drug composition solid substance contained within a cavity, where the particle has a broadest dimension of less than about 500 µm. The nanosized particle may include a plurality of particles, where each particle has substantially the same geometric shape. In some embodiments, the solid substance is granules or powder. The solid substance may be organic or inorganic.

According to some embodiments, the methods for fabricating nanosized particles can include placing a solid substance into a cavity in a mold, treating the solid substance so that the substance becomes substantially liquid, then hardening the liquified substance to make a particle, and removing the particle from the cavity.

According to some embodiments, methods for fabricating a nanosized particle include providing a mold, where the mold defines a cavity less than about 500 micron in average diameter, dispensing a solid substance to be molded onto the mold such that the solid substance at least partially fills the cavity, and hardening the substance in the cavity such that a particle is molded within the cavity. In alternative embodiments, the solid substance to be molded can be a granular, powder, combinations thereof, or the like. The solid substance may be organic or inorganic. Where the solid substance is granular, the methods can include chemically reacting the substance, sintering, phase change, curing, crosslinking, partial dissolution, recrystallization, combinations thereof, or the like to form a particle or particles from the initial solid substance.

In some embodiments, further processing can be applied to material deposited into a cavity of the mold. For example, granules positioned in a cavity can be partially dissolved then further processing can be applied to the partially dissolved granules to cure, evaporate, activate, or otherwise treat the partially dissolved granules and form a particle. Where the solid substance to be molded is granular, the methods can include the steps of treating the granules in the cavity to form at least a partial liquid and hardening the partial liquid. In alternative embodiments, granules introduced into the cavity can be treated to form a liquid and then hardened to form a particle that substantially takes the shape of the cavity. In some embodiments, treating the solid substance in the cavity can include dissolving the solid substance, melting the solid substance, chemically reacting the solid substance, curing, combinations thereof, or the like. According to some embodiments, hardening the liquified substance in the cavity can include cooling, evaporation, chemical processing, oxidation, reduction, photo-curing, thermal curing, crystallization, precipitation, combinations thereof, or the like.

According to some embodiments of the methods, the solid substance in the mold can be hardened by evaporation, a chemical process, treating the substance with UV light, a temperature change, treating the solid substance with thermal energy, curing, cross-linking, or the like. In some embodiments, the solid substance in the cavity is liquified, then hardened. In some embodiments, the methods include leaving the substrate in position on the mold to reduce evaporation of the substance from the cavity.

Some embodiments of the methods include harvesting the particle from the cavity after hardening the substance. According to alternative embodiments, the harvesting of nanosized particles includes applying an article that has affinity for the particles that is greater than an affinity between the particles and the mold. In some embodiments, the harvesting can further include contacting the particle with an adhesive substance, where adhesion between the particle and the adhesive substance is greater than adhesive force between the particle and the mold. In other embodiments, the harvesting substance can be selected from one or more of water, organic solvents, carbohydrates, epoxies, waxes, polyvinyl alcohol, polyvinyl pyrrolidone, polybutyl acrylate, polycyano acrylates, cellulose-containing polymers, and polymethyl methacrylate.

According to some embodiments, the composition can further include a plurality of particles, where the particles have a substantially uniform mass, are substantially monodisperse in mass, are substantially monodisperse in size or shape, or are substantially monodisperse in surface area. In some embodiments, multiple particles are produced in a single cavity. In some embodiments, multiple particles formed in single cavities can include a collection of particles that have substantially uniform mass from particle to particle and between particles of collections of particles formed in different cavities. In some embodiments, the plurality of particles have a normalized size distribution of between about 0.80 and about 1.20, between about 0.90 and about 1.10, between about 0.95 and about 1.05, between about 0.99 and about 1.01, between about 0.999 and about 1.001. According to some embodiments, the normalized size distribution is selected from the group of a linear size, a volume, a three dimensional shape, surface area, mass, and shape. In yet other embodiments, the plurality of particles includes particles that are monodisperse in surface area, volume, mass, three dimensional shape, or a broadest linear dimension.

According to some embodiments, the method includes additional processing steps after the particle is hardened. In some embodiments, a component of the particle is removed in an additional processing step. In some embodiments, the methods of removal can include chemical processing, a temperature change, dissolution, evaporation, reduction, extraction, combinations thereof, and the like. In some embodiments, a component is removed to increase surface area of the particle. In some embodiments, a component of the particle can be removed to increase purity of the particle. According to some embodiments, further processing can be etching, partially dissolving, physical processing, heating, cooling, combinations thereof, and the like.

BRIEF DESCRIPTION OF THE DRAWINGS

Reference is made to the accompanying drawings in which are shown illustrative embodiments of the presently disclosed subject matter, from which its novel features and advantages will be apparent.

DETAILED DESCRIPTION

The present invention broadly discloses discrete and uniform micro and/or nanometer sized particles fabricated from solid materials. In some embodiments, the solid materials used to form the discrete and uniform micro and/or nanometer sized particles includes granular solid materials, powdered solid materials, combinations thereof, or the like. In alternative embodiments, the micro and/or nanometer sized particles of the present invention are formed from smaller discrete and uniform micro and/or nanometer sized particles.

Figure 1:
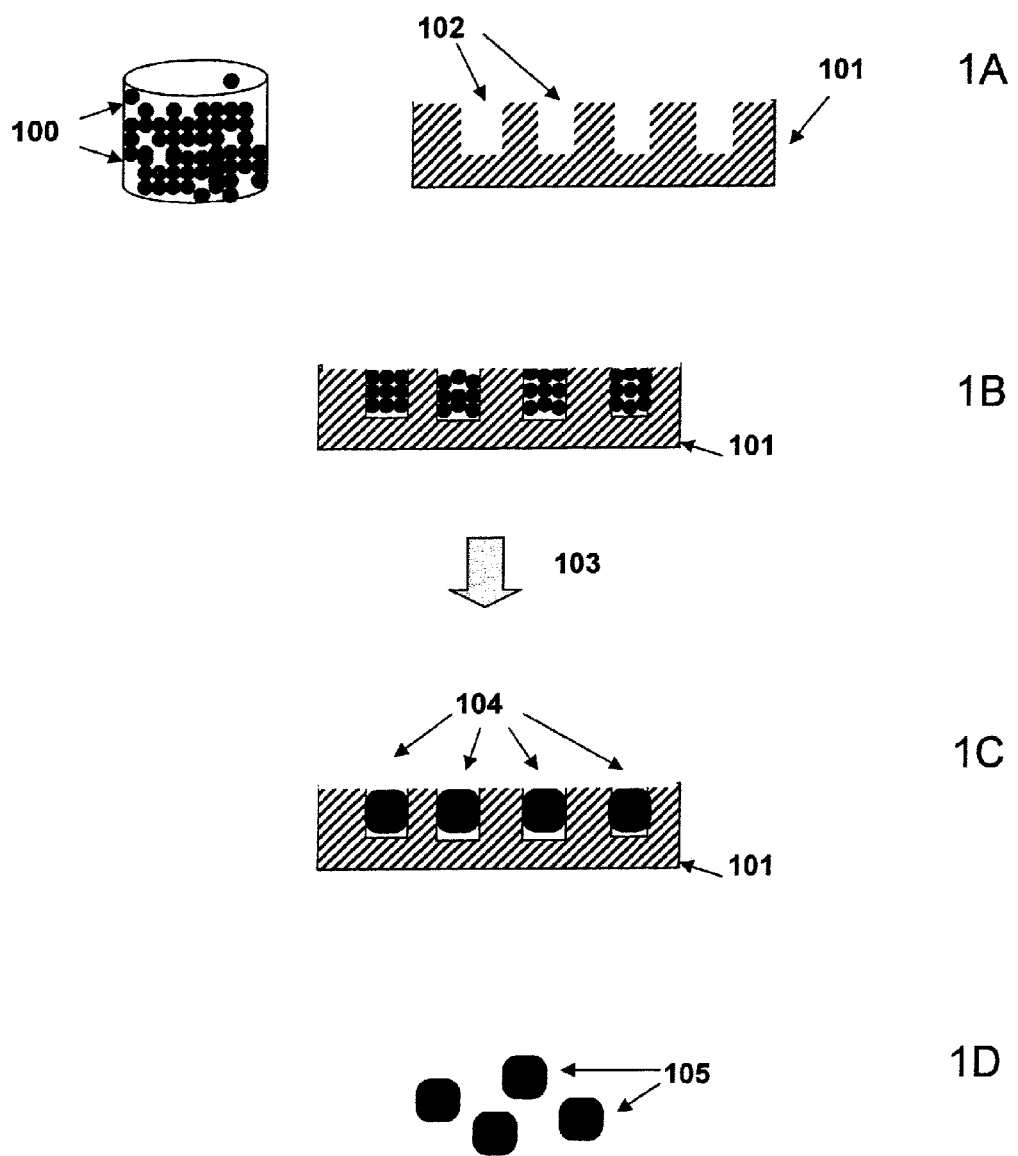
FIG. 1 shows a method of fabricating particles from a substance of finer particles, according to an embodiment of the present invention.

According to FIG. 1, a conventional mold 101 having micro and/or nanometer sized cavities or recesses 102 is provided. The mold 101 can be fabricated from a low surface energy elastomeric material such as FLUOROCUR™ resin (Liquidia Technologies, Inc.). Typically, mold 101 is fabricated by pouring the Fluorocur™ resin onto an etched wafer having predetermined etched shapes to be replicated. Once the Fluorocur™ resin is in communication with the etched wafer, the Fluorocur™ resin is cured by, for example, applying actinic radiation or heat to the Fluorocur™ resin. Once cured, the Fluorocur™ resin becomes an elastomeric mold 101 that can be physically removed from the etched wafer.

In some embodiments, cavities 102 have a surface energy below about 20 mN/m. According to another embodiment the surface energy of cavities 102 is between about 10 mN/m and about 20 mN/m. According to another embodiment, low surface energy of cavities 102 is between about 12 mN/m and about 15 mN/m. According to some embodiments, low surface energy of cavities 102 is less than about 15 mN/m. In some embodiments, the surface energy of cavities 102 is less than the surface energy of the solid powder or granular material that is being introduced into cavities 102.

Continuing with reference to FIG. 1, a substance introduced to cavities 102 of mold 101 is solid substance 100, as shown in FIG. 1B. Solid substance 100 can include one or more grains, one or more granules, powder, one or more fine particles, particles smaller than cavities 102 which are harvested from molds as disclosed in references incorporated herein by reference, combinations thereof, and the like. Solid substance 100 can be organic or inorganic. In some embodiments, solid substance 100 is included in a liquid. In some embodiments, solid substance 100 is suspended in a liquid. In alternative embodiments, solid substance 100 can be any pharmaceutical, drug, active, composition, agent, material, diagnostics, combination thereof, or the like disclosed or incorporated by reference herein.

In some embodiments, solid substance 100 is introduced to cavities 102 in granular form and remains granular until treated with treatment 103. In other embodiments, solid substance 100 is a granular substance included in a liquid prior to introduction to cavity 102. In alternative embodiments, solid substance 100 is granular when introduced to cavity 102 and is treated with treatment 103 to put solid substance 100 into a solution by melting, dissolving, or suspending solid substance 100 in a liquid after solid substance 100 is in cavity 102. Solid substance 100 can be subjected to liquids such as, but not limited to, solvents, water, solutions, mixtures, other liquids described herein, combinations thereof, and the like. According to yet further embodiments, solid substance 100 can be introduced into cavity 102 in a granular or powder form and let remain in such a form until treating.

Next, excess solid substance 100 that resides or remains on mold 101 and between cavities 102 is removed in some embodiments. According to some embodiments, removal of solid substance 100 from areas other than cavities 102 can include scraping, brushing, wiping, vibration, air flow, tilting the mold, washing the mold, washing the mold with a solvent that dissolves or partially dissolves solid substance 100, combinations thereof, or the like. According to other embodiments, excess solid substance 100 is removed by selective dissolution. According to other embodiments, excess solid substance 100 is removed by capillary action, suction, imbibition, absorption, or the like. In some embodiments, resulting particle 105 has a smaller volume than the mold or a smaller volume than a volume of the material introduced into the mold.

Next, as shown in FIG. 1C, a hardening treatment 104 can be applied to solid substance 100 to harden solid substance 100 and derive particle 105. According to some embodiments, hardening treatment 104 can be, for example, UV exposure, thermal exposure, oxidative processing, evaporation, crystallization, reductive processing, solubilization, precipitation, partial crystallization, combinations thereof, and the like. According to alternative embodiments, hardening treatment 104 can be applied to solid substance 100. According to such embodiments, hardening treatment 104 can be, but is not limited to, a chemical reaction, sintering, a phase change, curing, crosslinking, partial dissolution, recrystallization, precipitation, combinations thereof, or the like applied to solid substance 100 to form micro and/or nano-sized particle or particles 105 from the initial solid substance 100 that substantially mimics the size and shape of cavity 102. Following hardening treatment 104, solid substance 100 is formed into particles 105 that can be harvested from cavities 102 according to conventional methods.

According to some embodiments, after particles 105 are fabricated and removed from cavity 102 an additional processing can be applied to particles 105. In some embodiments, a component of particles 105 are removed in an additional processing step. In some embodiments, the methods of removal can include chemical processing, a temperature change, dissolution, evaporation, reduction, extraction, combinations thereof, and the like. In some embodiments, a component is removed to increase surface area of particles 105. In some embodiments, a component of particle 105 can be removed to increase purity of particles 105. According to some embodiments, further processing can be etching, partially dissolving, physical processing, heating, cooling, combinations thereof, and the like. In some embodiment, the further processing can increase a dissolution or absorption rate of particles 105.

According to some embodiments, because the Fluorocur™ resin replicates micro and/or nanosized structures and does not substantially shrink or swell upon curing and/or when in contact with most solvents, each cavity 102 has high fidelity and uniformity with respect to the structure it was replicated from. As a result, because each cavity 102 has high fidelity and uniformity among other cavities 102, particles 105 fabricated in cavities 102 have high fidelity and uniformity. According to some embodiments, particles 105 have a substantially uniform mass, are substantially monodisperse in mass, are substantially monodisperse in size or shape, and/or are substantially monodisperse in surface area. Accordingly, in some embodiments particles 105 formed in respective cavities 102 have a substantially uniform size distribution. In such embodiments, particles 105 formed in respective cavities 102, have a normalized size distribution of between about 0.80 and about 1.20, between about 0.90 and about 1.10, between about 0.95 and about 1.05, between about 0.99 and about 1.01, between about 0.999 and about 1.001, combinations thereof, and the like. Furthermore, in other embodiments particles 105 have a mono-dispersity. According to some embodiments, dispersity is calculated by averaging a dimension of particles 105. In some embodiments, the dispersity is based on, for example, surface area, length, width, height, mass, volume, porosity, combinations thereof, and the like.

According to some embodiments, particles 105 formed from mold 101 can each be less than about 10 µm in a dimension. In other embodiments, particles 105 can be each between about 10 µm and about 1 µm in dimension. In yet further embodiments, particles 105 are each less than about 1 µm in dimension. According to some embodiments particles 105 are each between about 1 nm and about 500 nm in a dimension. According to other embodiments, particles 105 are each between about 10 nm and about 200 nm in a dimension. In still further embodiments, particles 105 are each between about 80 nm and 120 nm in a dimension. According to still more embodiments particles 105 are each between about 20 nm and about 120 nm in dimension. The dimension of particles 105 can be a predetermined dimension, a cross-sectional diameter, a circumferential dimension, or the like.

According to some embodiments, particles 105 are formed having a predetermined shape, size, formulation, density, composition, surface features, spectral analysis, modulus, hardness, percent crystallinity, polymorph, or the like and can be less than about 200 µm in a given dimension (e.g. minimum, intermediate, or maximum dimension). In some embodiments, particle 105 is less than about 500 µm in a broadest dimension. In some embodiments, particle 105 is less than about 450 µm in a broadest dimension. In some embodiments, particle 105 is less than about 400 µm in a broadest dimension. In some embodiments, particle 105 is less than about 350 µm in a broadest dimension. In some embodiments, particle 105 is less than about 300 µm in a broadest dimension. In some embodiments, particle 105 is less than about 250 µm in a broadest dimension. In some embodiments, particle 105 is less than about 200 µm in a broadest dimension. In some embodiments, particle 105 is less than about 150 µm in a broadest dimension. In some embodiments, particle 105 is less than about 100 µm in a broadest dimension. In some embodiments, particle 105 is less than about 75 µm in a broadest dimension. In some embodiments, particle 105 is less than about 50 µm in a broadest dimension. In some embodiments, particle 105 is less than about 40 µm in a broadest dimension. In some embodiments, particle 105 is less than about 30 µm in a broadest dimension. In some embodiments, particle 105 is less than about 20 µm in a broadest dimension. In some embodiments, particle 105 is less than about 5 µm in a broadest dimension. In some embodiments, particle 105 is less than about 1 µm in a broadest dimension. In some embodiments, particle 105 is less than about 900 nm in a broadest dimension. In some embodiments, particle 105 is less than about 800 nm in a broadest dimension. In some embodiments, particle 105 is less than about 700 nm in a broadest dimension. In some embodiments, particle 105 is less than about 600 nm in a broadest dimension. In some embodiments, particle 105 is less than about 500 nm in a broadest dimension. In some embodiments, particle 105 is less than about 400 nm in a broadest dimension. In some embodiments, particle 105 is less than about 300 nm in a broadest dimension. In some embodiments, particle 105 is less than about 200 nm in a broadest dimension. In some embodiments, particle 105 is less than about 100 nm in a broadest dimension. In some embodiments, particle 105 is less than about 80 nm in a broadest dimension. In some embodiments, particle 105 is less than about 75 nm in a broadest dimension. In some embodiments, particle 105 is less than about 70 nm in a broadest dimension. In some embodiments, particle 105 is less than about 65 nm in a broadest dimension. In some embodiments, particle 105 is less than about 60 nm in a broadest dimension. In some embodiments, particle 105 is less than about 55 nm in a broadest dimension. In some embodiments, particle 105 is less than about 50 nm in a broadest dimension. In some embodiments, particle 105 is less than about 45 nm in a broadest dimension. In some embodiments, particle 105 is less than about 40 nm in a broadest dimension. In some embodiments, particle 105 is less than about 35 nm in a broadest dimension. In some embodiments, particle 105 is less than about 30 nm in a broadest dimension. In some embodiments, particle 105 is less than about 25 nm in a broadest dimension. In some embodiments, particle 105 is less than about 20 nm in a broadest dimension. In some embodiments, particle 105 is less than about 15 nm in a broadest dimension. In some embodiments, particle 105 is less than about 10 nm in a broadest dimension. In some embodiments, particle 105 is less than about 7 nm in a broadest dimension. In some embodiments, particle 105 is less than about 5 nm in a broadest dimension. In some embodiments, particle 105 is less than about 2 nm in a broadest dimension. In some embodiments, particle 105 is less than about 0.5 nm in a broadest dimension. In some embodiments, particle 105 is less than about 0.1 nm in a broadest dimension. According to some embodiments, particle 105 includes a broadest dimension between about 0.5 μm and about 10 μm. In another embodiment, particle 105 includes a broadest dimension between about 1 μm and about 7 μm. In another embodiment, particle 105 includes a broadest dimension between about 1.5 μm and about 5 μm. In another embodiment, particle 105 includes a broadest dimension between about 2 μm and about 4 μm. In another embodiment, particle 105 includes a broadest dimension between about 2.5 μm and about 3.5 μm.

According to other embodiments, particles 105 have predetermined regular and irregular shape and size configurations and can be made with the materials and methods of the presently disclosed subject matter. Examples of representative particle shapes that can be made using the materials and methods of the presently disclosed subject matter include, but are not limited to, non-spherical, spherical, viral shaped, bacteria shaped, cell shaped, rod shaped, chiral shaped, right triangle shaped, flat shaped, disc shaped, boomerang shaped, combinations thereof, and the like.

In other embodiments, particles 105 have predetermined geometric characteristics. According to some embodiments, geometric characteristics include a shape having two substantially flat and substantially parallel sides. In alternate embodiments, the predetermined geometric characteristics includes a predetermined radius of curvature, a predetermined angle between two sides of particle 105, a cuboidal shape, a conical shape, a spherical shape, a cylindrical shape, a rectangular shape, a cube shape, a cone shape, a sphere shape, a cylinder shape, a rectangle shape, combinations thereof, and the like. In some embodiments the predetermined geometric characteristic includes a predetermined radius of curvature. In other embodiments the predetermined geometric characteristic includes a substantially flat surface having a predetermined width, a substantially flat surface having a predetermined width, or two substantially flat surfaces, where the two substantially flat surfaces abut with a predetermined angle.

While not wishing to be bound by a particular theory, an example of producing a spherical or substantially spherical particle 105 includes using a mold fabricated from a non-wetting material or treating the surfaces of the mold with a non-wetting agent such that the material from which particle 105 will be formed does not wet the surfaces of the cavity. Because the material from which particle 105 will be formed cannot wet the surfaces of the mold, particle 105 has a greater affinity for itself than the surfaces of the cavity and thereby forms a rounded, curved, or substantially spherical shape. According to some embodiments, an equal amount of substance is evaporated from multiple cavities resulting in particles 105 in the cavities having a uniform or substantially uniform mass distribution therebetween.

According to other embodiments, one or more drugs can be included with particles 105 of the presently disclosed subject matter and can be found in Physician's Desk Reference, Thomson Healthcare, 59th Bk&Cr edition (2004), which is incorporated herein by reference in its entirety. According to other embodiments, one or materials can be included with presently disclosed particles 105; such materials include, but are not limited to the materials found in US Pharmacopeia and the Handbook of Pharmaceutical Excipients, which are incorporated herein by reference in their entirety.

According to some embodiments, solid substance 100 is a drug substance and processing the drug substance into a discrete size, shape, and/or controlled crystallinity can form variable polymorphs of the drug. Forming a drug from particles 105 of specific sizes, shapes and controlled crystallinity can increase the efficacy, efficiency, potency, solubility, and the like, of a drug substance. For more on polymorphs, see Lee et al., Crystallization on Confined Engineered Surfaces: A Method to Control Crystal Size and Generate Different Polymorphs, J. Am. Chem. Soc., 127 (43), 14982-14983, 2005, which is incorporated herein by reference in its entirety.

After solid substance 100 has been hardened, particles 105 are harvested from cavities 102. According to some embodiments particle 105 is harvested by contacting particle 105 with an article that has affinity for particles 105 that is greater than the affinity between particle 105 and cavity 102. By way of example, but not limitation, particle 105 is harvested by contacting particle 105 with an adhesive substance that adheres to particle 105 with greater affinity than affinity between particle 105 and cavity 102. According to some embodiments, the harvesting substance is, but is not limited to, water, organic solvents, carbohydrates, epoxies, waxes, polyvinyl alcohol, polyvinyl pyrrolidone, polybutyl acrylate, polycyano acrylates, polymethyl methacrylate, combinations thereof, and the like. According to still further embodiments a substance can be used for harvesting that forms a porous particle.

According to other embodiments, particles 105 are harvested by subjecting the particle/cavity combination and/or mold to a physical force or energy such that particles 105 are released from the cavity 102. In some embodiments the force is one or more of centrifugation, dissolution, vibration, ultrasonics, megasonics, gravity, flexure of the mold, suction, electrostatic attraction, electrostatic repulsion, magnetism, physical mold manipulation, combinations thereof, and the like.

According to some embodiments, particles 105 are purified after being harvested. In some embodiments particles 105 are purified from the harvesting substance. In some embodiments, the purifying can be, but is not limited to, centrifugation, separation, vibration, gravity, dialysis, filtering, sieving, electrophoresis, gas stream, magnetism, electrostatic separation, combinations thereof, and the like.

Representative materials useful in fabricating molds 101 in which particles 105 can be formed include elastomer-based materials. The elastomer-based materials include, but are not limited to, fluorinated elastomer-based materials, solvent resistant elastomer based materials, fluorinated elastomer-based materials that are liquid at room temperature, combinations thereof, and the like. As used herein, the term "solvent resistant" refers to a material, such as an elastomeric material that either does not swell or does not substantially swell nor dissolve or substantially dissolve in common hydrocarbon-based organic solvents, or reagents, or acidic or basic aqueous solutions. Representative fluorinated elastomer-based materials include but are not limited to fluoropolyether and perfluoropolyether (PFPE) based materials.

In some embodiments, the mold material is non-toxic, UV transparent, and highly gas permeable; and cures into a tough, durable, highly fluorinated elastomer with excellent release properties and resistance to swelling. The properties of these materials can be optimized over a wide range through the judicious choice of additives, fillers, reactive co-monomers, and functionalization agents. Such properties that are desirable to modify, include, but are not limited to, modulus, tear strength, surface energy, permeability, functionality, mode of cure, solubility and swelling characteristics, and the like. The non-swelling nature and easy release properties of the mold materials allows for nanostructures to be fabricated from nearly any material. Further, the presently disclosed subject matter can be expanded to large scale rollers or conveyor belt technology or rapid stamping that allow for the fabrication of nanostructures on an industrial scale.

In some embodiments, the material of mold 101 has a surface energy below about 20 mN/m. According to another embodiment the surface energy of mold 101 material is between about 10 mN/m and about 20 mN/m. According to another embodiment, low surface energy of the mold material is between about 12 mN/m and about 15 mN/m. According to some embodiments, low surface energy of the materials that form mold 101 is less than about 15 mN/m. In some embodiments, the surface energy of the materials that form mold 101 is less than the surface energy of the solid powder or granular material that is being introduced into mold 101.

In other embodiments, the material for forming the cavities can include, but is not limited to, a perfluoropolyether material, a fluoroolefin material, an acrylate material, a silicone material, a styrenic material, a fluorinated thermoplastic elastomer (TPE), a triazine fluoropolymer, a perfluorocyclobutyl material, a fluorinated epoxy resin, and a fluorinated monomer or fluorinated oligomer that can be polymerized or crosslinked by a metathesis polymerization reaction.

In some embodiments, the fluoroolefin material is made from monomers which include tetrafluoroethylene, vinylidene fluoride, hexafluoropropylene, 2,2-bis(trifluoromethyl)-4,5-difluoro-1,3-dioxole, a functional fluoroolefin, functional acrylic monomer, and a functional methacrylic monomer. In some embodiments, the silicone material includes a fluoroalkyl functionalized polydimethylsiloxane (PDMS). In some embodiments, the styrenic material includes a fluorinated styrene monomer. In some embodiments, the acrylate material includes a fluorinated acrylate or a fluorinated methacrylate. In some embodiments, the triazine fluoropolymer includes a fluorinated monomer. In some embodiments, the fluorinated monomer or fluorinated oligomer that can be polymerized or crosslinked by a metathesis polymerization reaction includes a functionalized olefin. In some embodiments, the functionalized olefin includes a functionalized cyclic olefin. According to an alternative embodiment, the mold material includes a urethane block, such as PFPE urethane tetrafunctional methacrylate materials, that can be used as the materials for the molds of the present invention.

From a property point of view, the exact properties of these materials can be adjusted by adjusting the composition of the ingredients used to make the materials. In particular the modulus can be adjusted from low (e.g., approximately 1 MPa) to multiple GPa by varying the cross-link density, for example.

Figure 2:
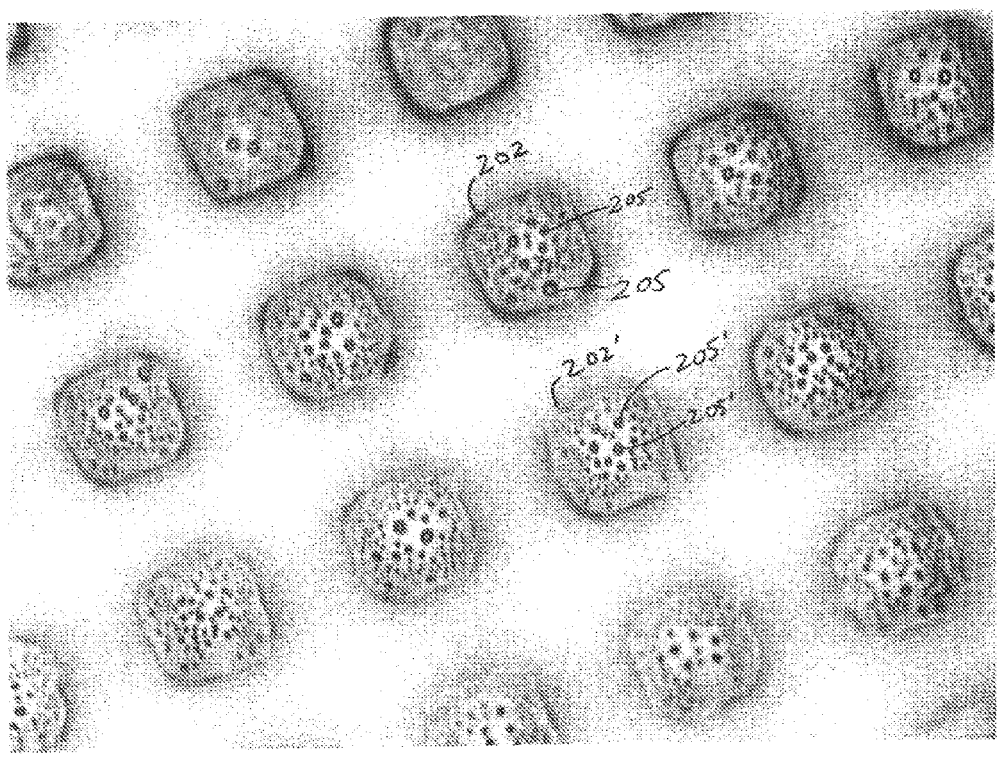
FIG. 2 shows multiple particles fabricated in individual cavities of a mold, according to an embodiment of the present invention.

Referring to FIG. 2, in some embodiments multiple particles 205 may be formed in single cavity 202. In some embodiments, multiple particles 205 formed in single cavity 202 can include a collection of particles 205 that each have substantially uniform mass. In one embodiment, particles 205 in cavity 202 have substantially uniform mass in comparison to particles 205' in cavity 202'. As set forth herein, particles 205 and 205' are derived from solid substance 100. Various treatment processes may result in multiple particles formed in a single cavity. Suitable treatment processes may include putting solid substance 100 into a solution by melting, dissolving, or suspending solid substance 100 in a liquid after solid substance 100 is in the cavity. In one embodiment, a hardening treatment may be applied to the liquid and solid substance, including for example, UV exposure, thermal exposure, oxidative processing, evaporation, crystallization, reductive processing, solubilization, precipitation, partial crystallization, combinations thereof, and the like. According to alternative embodiments, hardening treatment can be applied to solid substance 100. According to such embodiments, a hardening treatment can be, but is not limited to, a chemical reaction, sintering, a phase change, curing, crosslinking, partial dissolution, recrystallization, precipitation, combinations thereof, or the like applied to solid substance 100 to form micro and/or nanosized particles from initial solid substance 100.

Unless otherwise defined, all technical and scientific terms used herein have the same meaning as commonly understood by one of ordinary skill in the art to which this presently described subject matter belongs. All publications, patent applications, patents, and other references mentioned herein are incorporated by reference in their entirety. Throughout the specification and claims, a given chemical formula or name shall encompass all optical and stereoisomers, as well as racemic mixtures where such isomers and mixtures exist.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter.

Fabrication of Drug Particles by Recrystallization

A patterned perfluoropolyether (PFPE) mold can be generated by casting a PFPE-dimethacrylate (PFPE-DMA) containing 2,2-diethoxyacetophenone over a silicon substrate patterned with uniform posts. The coated master will then be subjected to a nitrogen purge while the PFPE film is cured with 365 nm radiation for 5 minutes. The fully cured PFPE-DMA mold can then be peeled from the silicon master leaving a mold with uniform cavity replicates of the uniform posts of the silicon substrate. An emulsion of solid drug product and water will be applied to the patterned surface of the PFPE mold. The emulsion will fill the cavities of the mold and then be dried to leave solid granules of drug product in the cavities. A solvent, such as ethanol, will be laminated between the PFPE mold and a polyethylene sheet to partially dissolve the drug product. The laminate will then be heated to coalesce the solid drug granules. The combination can then be cooled to room temperature. The polyethylene sheet can then be removed and a single substantially uniform particle should exist in each cavity.

Fabrication of Inorganic Particles

A patterned perfluoropolyether (PFPE) mold can be generated by casting a PFPE-dimethacrylate (PFPE-DMA) containing 2,2-diethoxyacetophenone over a silicon substrate patterned with uniform posts. The coated master can then be subjected to a nitrogen purge while the PFPE film is cured with 365 nm radiation for 5 minutes. The fully cured PFPE-DMA mold will then be peeled from the silicon master leaving a mold with uniform cavity replicates of the uniform posts of the silicon substrate. A powder of fine metal grains will be applied to the patterned surface of the PFPE mold, where by the grains will be allowed to settle into the mold cavities. A coalescing solution will be laminated between the PFPE mold and a polyethylene sheet. The sheet is not required, but can help to minimize solvent evaporation. The laminate can then be heated to coalesce the metal grains and then cooled. The polyethylene sheet can then be removed and a single metal particle should be revealed in each cavity.

It will be understood that various details of the presently disclosed subject matter can be changed without departing from the scope of the presently disclosed subject matter. Furthermore, the foregoing description is for the purpose of illustration only, and not for the purpose of limitation.

What is claimed is:

1. A method of fabricating a nanosized particle, comprising:
   introducing a solid substance to a cavity defined in a mold, wherein the cavity comprises a predetermined shape and has a broadest dimension less than about 500 μm;
   forming a particle from the solid substance in the cavity, wherein the particle substantially mimics a shape of the cavity; and
   removing the particle from the cavity.

2. The method of claim 1, wherein the mold comprises a fluoropolymer.

3. The method of claim 1, wherein the mold comprises a perfluoropolyether.

4. The method of claim 1, wherein the solid substance is organic.

5. The method of claim 1, wherein the solid substance is granular.

6. The method of claim 1, wherein the solid substance is a powder.

7. The method of claim 1, wherein forming comprises dissolving, partially dissolving, melting, sintering, chemically treating, inducing a phase change, cross-linking, crystallization, partial crystallization, precipitation, evaporation, cooling, heating, oxidation, reduction, photo-curing, thermal curing, recrystallization, or partial recrystallization.

8. The method of claim 1, further comprising, after removing, processing the particle.

9. The method of claim 8, wherein the processing of the particle comprises removing material from the particle, increasing surface area, increasing purity, etching, partial dissolution, physical processing, heating, cooling, chemical processing, evaporation, reduction, or extraction.

10. The method of claim 1, wherein the solid substance comprises a drug component.

11. The method of claim 1, wherein the solid substance is selected from the group consisting of a pharmaceutical, an active agent, a drug, a biologic molecule, a virus, a binder, and combinations thereof.

* * * * *